US00PP21810P2

(12) United States Plant Patent

Kanaya

(10) Patent No.: US PP21,810 P2
(45) Date of Patent: Mar. 22, 2011

(54) *CALIBRACHOA* PLANT NAMED 'SUNCALHO'

(50) Latin Name: ***Calibrachoa* sp.**
Varietal Denomination: Suncalho

(75) Inventor: Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/590,015

(22) Filed: Oct. 30, 2009

(51) Int. Cl.
*A01H 5/00* (2006.01)

(52) U.S. Cl. ..... Plt./413
(58) Field of Classification Search ..... Plt./413

See application file for complete search history.

*Primary Examiner*—June Hwu
(74) *Attorney, Agent, or Firm*—C. A. Whealy

(57) ABSTRACT

A new and distinct cultivar of *Calibrachoa* plant named 'Suncalho', characterized by its compact and mounding plant habit; vigorous growth habit; freely branching and flowering plant habit; long flowering period; large white-colored flowers; and good garden performance.

1 Drawing Sheet

Botanical designation: *Calibrachoa* sp.
Cultivar denomination: 'SUNCALHO'.

BACKGROUND OF THE INVENTION

The present invention relates to a new and distinct cultivar of *Calibrachoa* plant, botanically known as *Calibrachoa* sp. and hereinafter referred to by the name 'Suncalho'.

The new *Calibrachoa* plant is a product of a planned breeding program conducted by the Inventor in Higashiomi, Shiga, Japan. The objective of the breeding program is to develop new mounding and freely-branching *Calibrachoa* plants with attractive and unique flower coloration.

The new *Calibrachoa* plant originated from a cross-pollination conducted by the Inventor in Higashiomi, Shiga, Japan in April, 2006 of a proprietary selection of *Calibrachoa* sp. identified as code number 2666-1, not patented, as the female, or seed, parent with a proprietary selection of *Calibrachoa* sp. identified as code number 3135-2, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in September, 2007.

Asexual reproduction of the new *Calibrachoa* plant by vegetative cuttings in a controlled greenhouse environment in Higashiomi, Shiga, Japan since October, 2007, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Suncalho'. These characteristics in combination distinguish 'Suncalho' as a new and distinct cultivar of *Calibrachoa:*

1. Compact and mounding plant habit.

2. Vigorous growth habit.
3. Freely branching and flowering plant habit.
4. Long flowering period.
5. Large white-colored flowers.
6. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* have larger flowers than plants of the female parent selection.
2. Plants of the new *Calibrachoa* and the female parent selection differ in flower color as plants of the female parent selection have light pink-colored flowers.

Plants of the new *Calibrachoa* can be compared to plants of the male parent selection. Plants of the new *Calibrachoa* differ primarily from plants of the male parent selection in the following characteristics:

1. Plants of the new *Calibrachoa* are more compact and mounding than plants of the male parent selection.
2. Plants of the new *Calibrachoa* have larger flowers than plants of the male parent selection.
3. Plants of the new *Calibrachoa* and the male parent selection differ in flower color as plants of the male parent selection have vivid pink-colored flowers.

Plants of the new *Calibrachoa* can also be compared to plants of 'Sunbelho', disclosed in U.S. Plant Pat. No. 15,764. In side-by-side comparisons conducted in Higashiomi, Shiga, Japan, plants of the new *Calibrachoa* and 'Sunbelho' differed primarily in the following characteristics:

1. Plants of the new *Calibrachoa* were more compact and mounding than plants of 'Sunbelho'.
2. Plants of the new *Calibrachoa* were more freely branching than plants of 'Sunbelho'.
3. Plants of the new *Calibrachoa* had shorter internodes than plants of 'Sunbelho'.
4. Plants of the new *Calibrachoa* had broader leaves than plants of 'Sunbelho'.
5. Plants of the new *Calibrachoa* had larger flowers than plants of 'Sunbelho'.

6. Plants of the new *Calibrachoa* had broader sepals than plants of 'Sunbelho'.

BRIEF DESCRIPTION OF THE PHOTOGRAPHS

The accompanying colored photographs illustrate the overall appearance of the new *Calibrachoa*, showing the colors as true as it is reasonably possible to obtain in colored reproductions of this type. Colors in the photographs may differ slightly from the color values cited in the detailed botanical description which accurately describe the colors of the new *Calibrachoa*.

The photograph at the top of the sheet comprises a side perspective view of a typical flowering plant of 'Suncalho' grown in a container.

The photograph at the bottom of the sheet is a close-up view of typical flowers of 'Suncalho'.

DETAILED BOTANICAL DESCRIPTION

The aforementioned photographs and following observations, measurements and values describe plants grown in 15-cm containers in Higashiomi, Shiga, Japan, under commercial practice during the spring and early summer in an outdoor nursery. During the production of the plants, day temperatures averaged 23° C. and night temperatures averaged 13° C. Plants were four and five months old when the description and photographs, respectively, were taken. In the following description, color references are made to The Royal Horticultural Society Colour Chart, 2001 Edition, except where general terms of ordinary dictionary significance are used.

Botanical classification: *Calibrachoa* sp. 'Suncalho'.

Parentage:

*Female, or seed, parent.*—Proprietary selection of *Calibrachoa* sp. identified as code number 2666-1, not patented.

*Male, or pollen, parent.*—Proprietary selection of *Calibrachoa* sp. identified as code number 3135-2, not patented.

Propagation:

*Type.*—By vegetative cuttings.

*Time to initiate roots.*—About one week at 15° C. to 20° C.

*Time to produce a rooted young plant.*—About three weeks at 15° C. to 20° C.

*Root description.*—Fibrous; white in color.

*Rooting habit.*—Freely branching.

Plant description:

*Plant and growth habit.*—Compact and mounding plant habit; freely branching habit with numerous lateral branches developing per plant; pinching is not required, but will enhance lateral branch development; vigorous growth habit.

*Plant height.*—About 14.8 cm.

*Plant diameter.*—About 43.4 cm.

Lateral branch description:

*Length.*—About 20.2 cm.

*Diameter.*—About 2 mm.

*Internode length.*—About 9 mm.

*Strength.*—Strong.

*Aspect.*—Upright to outward.

*Texture.*—Pubescent.

*Color.*—Close to 144B.

Foliage description:

*Arrangement.*—Alternate, simple.

*Length.*—About 4.7 cm.

*Width.*—About 2.3 cm.

*Shape.*—Elliptic.

*Apex.*—Broadly acute.

*Base.*—Obtuse to cuneate.

*Margin.*—Entire.

*Texture, upper and lower surfaces.*—Pubescent.

*Venation pattern.*—Pinnate; reticulate.

*Color.*—Developing leaves, upper surface: Close to 144A. Developing leaves, lower surface: Close to 144B. Fully expanded leaves, upper surface: Close to 137A; venation, close to 145A. Fully expanded leaves, lower surface: Close to 137C; venation, close to 145A.

*Petiole.*—Length: About 3 mm. Diameter: About 1.7 mm. Texture, upper and lower surfaces: Pubescent. Color, upper and lower surfaces: Close to 145A.

Flower description:

*Flower arrangement and habit.*—Single salverform flowers arising from upper leaf axils; freely flowering habit with usually about 89 open flowers per plant at one time; flowers face upright or outwardly.

*Fragrance.*—None detected.

*Natural flowering season.*—Early flowering habit, plants of the new *Calibrachoa* initiate and develop flowers about three to four weeks after planting; long flowering period; flowering commences naturally during the spring and plants flower continuously throughout the summer until late autumn in Japan.

*Flower longevity.*—Individual flowers last about seven to ten days on the plant; flowers not persistent.

*Flower diameter.*—About 4.3 cm.

*Flower length (depth).*—About 3 cm.

*Throat diameter.*—About 1.2 cm.

*Tube length.*—About 2 cm.

*Tube diameter.*—About 1.9 mm.

*Flower bud.*—Shape: Cylindrical. Length: About 2.5 cm. Diameter: About 7.6 mm. Color: Close to 150D.

*Corolla.*—Arrangement: Five petals fused at the base and opening into a flared trumpet. Petal length from throat: About 1.6 cm. Petal width: About 2.1 cm. Petal shape: Spatulate. Petal apex: Rounded with truncate tendencies. Petal margin: Entire. Petal texture, upper and lower surfaces: Smooth, glabrous. Throat texture: Smooth, glabrous. Tube texture: Pubescent. Color: Petal, when opening, upper and lower surfaces: Close to 155B. Petal, fully opened, upper and lower surfaces: Close to 155B. Throat: Close to 9A; venation, close to 144B. Tube: Close to 154B; venation, close to 145B.

*Calyx.*—Arrangement: One star-shaped calyx tube with five sepals fused at the base. Sepal length: About 8.1 mm to 14 mm. Sepal width: About 4.2 mm. Sepal shape: Lanceolate. Sepal apex: Acute. Sepal margin: Entire. Sepal texture, upper and lower surfaces: Pubescent. Color, immature, upper and lower surfaces: Close to 137B. Color, mature, upper surface: Close to 137B. Color, mature, lower surface: Close to 138B.

*Peduncles.*—Length: About 2 cm. Diameter: About 0.8 mm. Angle: Upright to outwardly. Strength: Strong. Texture: Pubescent. Color: Close to 144B.

*Reproductive organs.*—Stamens: Quantity/arrangement: Five per flower. Stamen length: About 6.3 mm to 12 mm. Anther shape: Ellipsoidal. Anther size:

About 1.3 mm by 1.3 mm. Anther color: Close to 6D. Pollen amount: Moderate. Pollen color: Close to 8C. Pistils: Quantity: One per flower. Pistil length: About 7.9 mm. Style color: Close to 145B. Stigma shape: Transversely ellipsoidal. Stigma color: Close to 144B. Ovary color: Close to 145B. Seed/fruit: Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Suncalho' as illustrated and described.

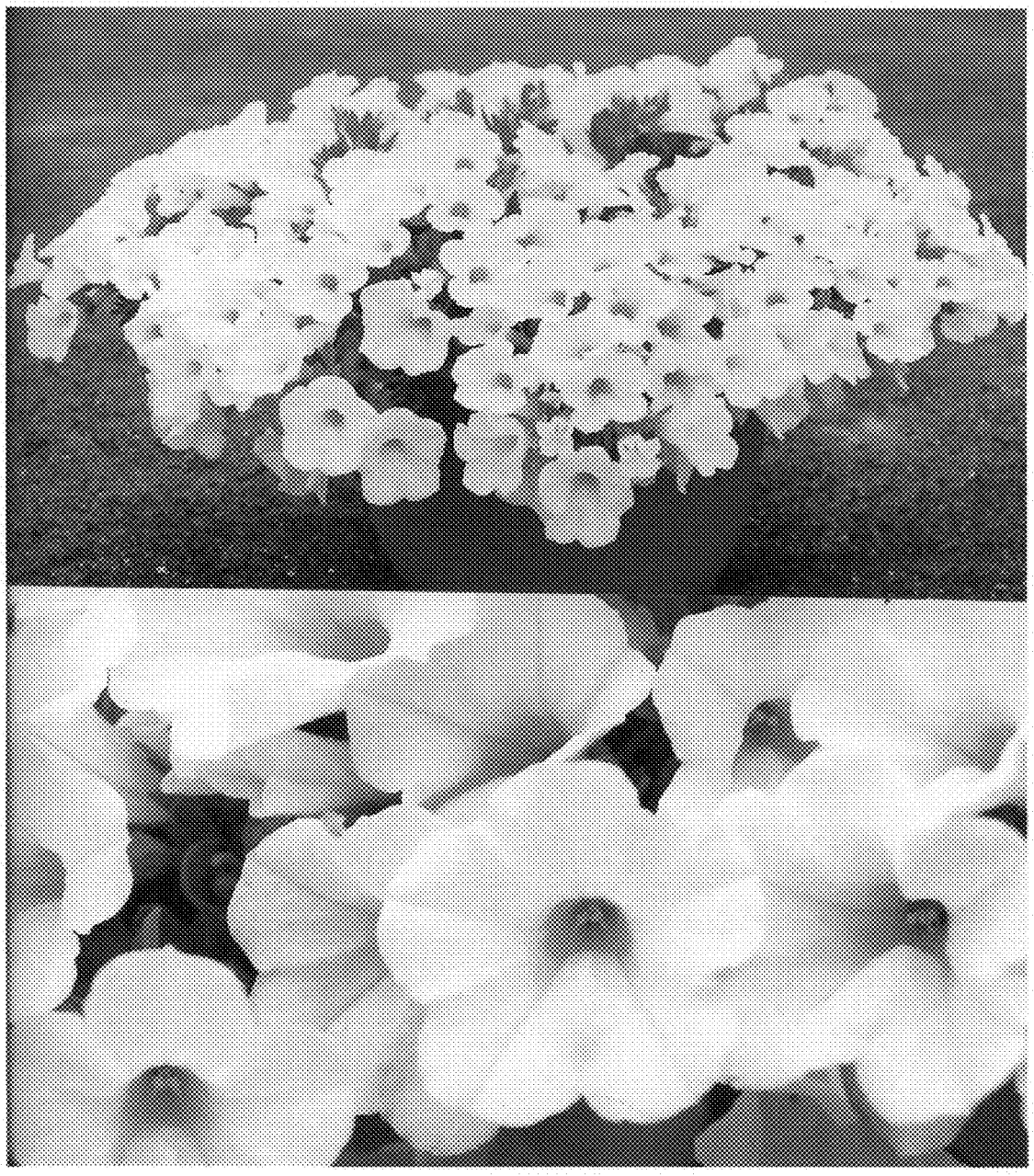

* * * * *